United States Patent [19]

Kamei et al.

[11] Patent Number: 5,369,206
[45] Date of Patent: Nov. 29, 1994

[54] METHOD FOR THE PREPARATION OF AN ORGANOPOLYSILOXANE POLYMERIZABLE AT A SINGLE MOLECULAR CHAIN END

[75] Inventors: Masanao Kamei; Tomohisa Suzuki, both of Gunma, Japan

[73] Assignee: Shin-Etsu Chemical Co., Ltd., Tokyo, Japan

[21] Appl. No.: 189,386

[22] Filed: Jan. 31, 1994

[30] Foreign Application Priority Data

Jan. 29, 1993 [JP] Japan .................................. 5-034734

[51] Int. Cl.$^5$ .............................................. C08G 77/20
[52] U.S. Cl. .................................... 528/32; 556/440; 556/459; 556/469; 528/34; 528/38; 528/41
[58] Field of Search .................. 528/38, 41, 32, 34; 556/440, 459, 469

[56] References Cited

U.S. PATENT DOCUMENTS

| | | | |
|---|---|---|---|
| 4,737,563 | 4/1988 | Arai et al. | 528/31 |
| 5,049,635 | 9/1991 | Inoue | 528/33 |
| 5,288,890 | 2/1994 | Inomata et al. | 556/440 |

*Primary Examiner*—Melvyn I. Marquis
*Attorney, Agent, or Firm*—Millen, White, Zelano & Branigan

[57] ABSTRACT

A diorganopolysiloxane terminated only at one of the molecular chain ends with a (meth)acryloxyalkyl group bonded to the terminal silicon atom is prepared, instead of the prior art method in which a diorganopolysiloxane obtained by the anionic ring-opening living polymerization reaction of, for example, hexamethyl cyclotrisiloxane by using a lithium catalyst is subjected to a desalinating condensation reaction with a (meth)acryloxyalkyl dimethyl chlorosilane, by a novel method in which the diorganopolysiloxane obtained by the anionic ring-opening living polymerization reaction of, for example, hexamethyl cyclotrisiloxane is hydrolyzed and the thus obtained monofunctionally silanol-terminated diorganopolysiloxane is reacted with a (meth)acryloxyalkyl dimethyl dialkylamino silane to effect a deamination reaction. This method is advantageous in that the relatively narrow molecular weight distribution of the diorganopolysiloxane obtained by the anionic living polymerization is not affected and retained as such in the deamination reaction while not in the prior art method.

5 Claims, No Drawings

METHOD FOR THE PREPARATION OF AN ORGANOPOLYSILOXANE POLYMERIZABLE AT A SINGLE MOLECULAR CHAIN END

BACKGROUND OF THE INVENTION

The present invention relates to a method for the preparation of an organopolysiloxane ethylenically polymerizable only at a single molecular chain end or, more particularly, to an efficient method for the preparation of an organopolysiloxane having a straightly linear molecular structure of a controllable molecular weight or molecular weight distribution and having an ethylenically unsaturated polymerizable linkage only at one of the molecular chain ends.

As is known, organopolysiloxanes having ethylenical polymerizability only at a single molecular chain end are widely used in the polymer industry because a copolymer of such an organopolysiloxane and (meth)acrylic acid or an ester thereof as well as other vinyl monomers is imparted with various desirable properties such as water-repellency, heat resistance, weatherability, abrasion resistance and the like.

A method for the preparation of such a polymerizable organopolysiloxane is disclosed in Japanese Patent Publication No. 59-78236, according to which a cyclic organopolysiloxane oligomer such as hexamethyl cyclotrisiloxane is subjected to a ring-opening living polymerization in the presence of an anionic polymerization initiator such as organolithium compounds, alkali metal hydroxides, alkali metal alkoxides and alkali metal silanolates and the thus obtained organopolysiloxane is subjected to a desalinating condensation reaction with an ω-(meth)acryloxyalkyl dichlorosilane.

In this method, however, formation of hydrogen chloride is unavoidable because the chlorosilane reactant must be used in an excess amount over stoichiometry so that the hydrogen chloride acts as a catalyst to promote the siloxane rearrangement equilibrium reaction as a consequence of scission of the siloxane linkages leading to broadening of the relatively narrow molecular weight distribution of the organopolysiloxane as obtained by the living polymerization.

SUMMARY OF THE INVENTION

The present invention accordingly has an object to provide a novel and efficient method for the preparation of an organopolysiloxane ethylenically polymerizable only at a single molecular chain end without the above described problems in the prior art methods relative to the controllability of the molecular weight or molecular weight distribution.

Thus, the method of the present invention for the preparation of an organopolysiloxane ethylenically polymerizable only at a single molecular chain end represented by the general formula

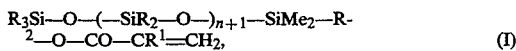

in which Me is a methyl group, R is, each independently from the others, an alkyl group having 1 to 6 carbon atoms or a phenyl group, $R^1$ is a hydrogen atom or a methyl group, $R^2$ is a divalent hydrocarbon group having 1 to 6 carbon atoms and n is zero or a positive integer not exceeding 1000, comprises:

reacting an organopolysiloxane having a silanolic hydroxy group only at a single molecular chain end as represented by the general formula

in which each symbol has the same meaning as defined above, with a (meth)acryloxyalkyl dimethyl dialkylamino silane compound represented by the general formula

in which Me, $R^1$ and $R^2$ each have the same meaning as defined above and $R^3$ is an alkyl group having 1 to 6 carbon atoms.

DETAILED DESCRIPTION OF THE PREFERRED EMBODIMENTS

As is described above, the present invention provides a novel method for the preparation of an organopolysiloxane ethylenically polymerizable only at a single molecular chain end as represented by the above given general formula (I), which can be easily obtained by the deamination reaction of an organopolysiloxane having a silanolic hydroxy group only at a single molecular chain end as represented by the general formula (II) with the aminosilane compound represented by the above given general formula (III).

The starting organopolysiloxane terminated only at a single molecular chain end with a silanolic hydroxy group is represented by the general formula (II), in which each R is, independently from the others, a monovalent hydrocarbon group selected from the class consisting of alkyl groups having 1 to 6 carbon atoms such as methyl, ethyl, propyl, butyl and hexyl groups and phenyl group and the subscript n is zero or a positive integer not exceeding 1000.

The above defined starting organopolysiloxane of the general formula (II) can be prepared, for example, by the anionic ring-opening living polymerization of a cyclic diorganosiloxane oligomer such as hexamethyl cyclotrisiloxane in the presence of an anionic living polymerization initiator such as an alkyl lithium, e.g., methyl lithium, ethyl lithium, propyl lithium and n-butyl lithium, alkali metal hydroxide, e.g., potassium hydroxide, sodium hydroxide and lithium hydroxide, alkali metal alkoxide, e.g., lithium methoxide, lithium ethoxide, sodium methoxide, potassium methoxide and potassium ethoxide, alkali metal silanolate, e.g., trimethyl and triethyl silanolates of potassium, sodium and lithium, and the like to prepare a diorganopolysiloxane terminated at one molecular chain end with a lithium silanolate group followed by a hydrolysis treatment of the same with an excess amount of water.

The above mentioned anionic ring-opening living polymerization of a cyclic diorganosiloxane oligomer with an anionic living polymerization initiator is carried out preferably in a solution with a polar organic solvent such as tetrahydrofuran, diethyl ether, 1,4-dioxane and the like with optional admixture of other organic solvents such as dimethyl sulfoxide, N,N-dimethyl formamide and the like at a temperature in the range from 0° to 70° C. or, preferably, from 10° to 25° C. The polymerization reaction is complete usually within 2 to 24 hours or, in most cases, within 3 to 5 hours. The average molecular weight of the thus obtained diorganopolysiloxane having functionality only at one molecular chain end, which has a relatively uniform molecular weight distribution, can be controlled by selecting the molar ratio of the starting cyclic diorganosiloxane oligomer and the anionic living polymerization initiator.

The (meth)acryloxyalkyl dimethyl amino silane as the reactant to be reacted with the above described starting monofunctional diorganopolysiloxane is represented by the above given general formula (III), in which $R^3$ is an alkyl group having 1 to 6 carbon atoms such as methyl, ethyl, propyl, butyl and hexyl groups and $R^2$ is a divalent hydrocarbon group having 1 to 6 carbon atoms such as methylene, ethylene, propylene and butylene groups.

Examples of the above defined (meth)acryloxyalkyl dimethyl dialkylamino silane include: 3-methacryloxypropyl dimethyl dimethylamino silane; 3-methacryloxypropyl dimethyl methylethylamino silane; 3-methacryloxypropyl dimethyl diethylamino silane; 3-methacryloxypropyl dimethyl ethylbutylamino silane; methacryloxymethyl dimethyl dihexylamino silane; methacryloxymethyl dimethyl dimethylamino silane; 3-acryloxypropyl dimethyl dimethylamino silane; 3-acryloxypropyl dimethyl methylethylamino silane; acryloxymethyl dimethyl diethylamino silane; acryloxymethyl dimethyl ethylbutylamino silane; and the like.

These ω-(meth)acryloxyalkyl dimethyl dialkylamino silane compounds can be synthesized, for example, by the dehydrochlorination reaction between an ω-(meth)acryloxyalkyl dimethyl chlorosilane and a dialkyl amine in the presence of an acid acceptor.

In the reaction of the above described (meth)acryloxyalkyl dimethyl dialkylamino silane with the monofunctional silanol-terminated diorganopolysiloxane, the silane compound is used in an amount in the range from 1.0 to 1.5 moles or, preferably, from 1.0 to 1.1 moles per mole of the diorganopolysiloxane reactant. The reaction of these reactants can be performed without using any organic solvents but it is preferable that the reactants are dissolved in an organic solvent and the reaction is performed in the solution. Suitable organic solvents include those having no active hydrogen such as hydrocarbon solvents, e.g., hexane, toluene and xylene, ether solvents, e.g., tetrahydrofuran, diethyl ether, dibutyl ether and dioxane, and the like. The reaction temperature should be in the range from room temperature to 110° C. or, preferably, from 50° to 70° C. According to this method, the organopolysiloxane under reaction is substantially free from the problem of siloxane chain scission so that the average molecular weight and the molecular weight distribution of the starting diorganopolysiloxane are not affected by the deamination reaction to give the desired diorganopolysiloxane represented by the general formula (I) in a good yield.

In the following, the method of the present invention is described in more detail by way of examples and comparative examples as preceded by the description of the synthetic procedure for the preparation of 3-methacryloxypropyl dimethyl diethylamino silane.

Synthesis of 3-methacryloxypropyl dimethyl diethylamino silane

Into a four-necked glass flask of 500 ml capacity equipped with a reflux condenser, thermometer, dropping funnel and stirrer were introduced 80 g of diethylamine and 150 g of toluene to form a solution and, while the solution is chilled with ice, 110 g of 3-methacryloxypropyl dimethyl chlorosilane were added dropwise thereinto. After completion of the dropwise addition of the silane compound, the reaction mixture in the flask was agitated for 24 hours at room temperature followed by filtration to remove the precipitates of diethylamine hydrochloride. The filtrate was, after stripping of toluene, subjected to distillation under reduced pressure to give 93 g of a liquid product boiling at 89° to 91° C. under a pressure of 1 mmHg. This product was analyzed by the methods of $^1$H-NMR analysis and infrared absorption spectrophotometric analysis to give the results shown below from which it could be identified to be 3-methacryloxypropyl dimethyl diethylamino silane. The above mentioned yield of the product corresponds to 73% of the theoretical value.

$^1$H-NMR analysis, δ 0.2. ppm (s, 6H, Si—CH$_3$) 0.7 ppm (m, 2H, Si—CH$_2$—) 1.1 ppm (t, 6H, C—CH$_3$) 1.8 ppm (m, 2H, C—CH$_2$—C) 2.0 ppm (m, 3H, C—CH$_3$) 2.9 ppm (q, 4H, N—CH$_2$—) 4.1 ppm (t, 2H, O—CH$_2$—) 5.5 ppm (m, 2H, =CH$_2$) Infrared absorption spectrophotometric analysis 1250 cm$^{-1}$; 1730 cm$^{-1}$; 1800 cm$^{-1}$; 2950 cm$^{-1}$

EXAMPLE 1

Into a three-necked glass flask of 50 ml capacity equipped with a stirrer, thermometer and dropping funnel were introduced 4.95 g of trimethyl silanol and 5 g of toluene to form a solution into which 12.9 g of 3-methacryloxypropyl dimethyl diethylamino silane prepared above were added dropwise at room temperature and the reaction mixture was heated at 70° C. and agitated for 3 hours. Thereafter, the reaction mixture was freed from toluene and subjected to distillation under reduced pressure to give 9.8 g of a liquid product boiling at 85° to 86° C. under a pressure of 1 mmHg. This liquid product was analyzed by the method of $^1$H-NMR analysis to give the results shown below, from which it could be identified to be 1,1,1,3,3-pentamethyl-3-(3-methacryloxypropyl) disiloxane. The above mentioned yield of the product corresponds to 72% of the theoretical value.

$^1$H-NMR analysis, δ 0.1 ppm (s, 9H, Si—CH$_3$) 0.2 ppm (s, 6H, Si—CH$_3$) 0.7 ppm (m, 2H, C—CH$_2$—) 1.8 ppm (m, 2H, C—CH$_2$—C) 2.0 ppm (m, 3H, C—CH$_3$) 4.1 ppm (t, 2H, O—CH$_2$—)
5.5 and 6.1 ppm (m, 2H, =CH2)

EXAMPLE 2

Into a flask of 5 liter capacity equipped with a stirrer, thermometer and reflux condenser were introduced 3000 g of dehydrated tetrahydrofuran and 1200 g of hexamethyl cyclotrisiloxane to form a solution into which 26 g of lithium trimethyl silanolate and 300 g of dehydrated tetrahydrofuran were added and the mixture was agitated for 4 hours at room temperature. The mixture was then washed with water to remove a part of the tetrahydrofuran followed by phase separation and dehydration of the organic phase. The thus obtained diorganopolysiloxane had a number-average molecular weight $M_n$ of 6200 and weight-average molecular weight $M_w$ of 6660.

The dehydrated organic mixture was heated at 60° C. and 76.5 g of 3-methacryloxypropyl dimethyl diethylamino silane prepared above were added dropwise thereto and the mixture was agitated at the same temperature for 2 hours. Thereafter, the mixture was subjected to distillation under reduced pressure at 120° C. to remove the solvent so that 1210 g of a liquid product was obtained. This liquid product was subjected to the gel-permeation chromatographic analysis and infrared spectrophotometric analysis to give the results shown below, from which the product could be identified to be a dimethyl polysiloxane terminated at a single molecular chain end with a 3-methacryloxypropyl group. The degree of molecular weight dispersion $M_w/M_n$ indicated that the product diorganopolysiloxane had a very narrow molecular weight distribution.

Molecular weight by gel-permeation chromatography (reference made to polystyrenes)

$M_n$: 6480
$M_w$: 6900
$M_w/M_n$: 1.06

Infrared absorption spectrophotometry
1000–1100 cm$^{-1}$ (Si—O—Si)
1250 cm$^{-1}$ (Si—C)
1730 cm$^{-1}$ (C=O)
2950 cm$^{-1}$ (CH—)

Comparative Example 1

Into a three-necked flask of 100 ml capacity equipped with a stirrer, thermometer and reflux condenser was introduced a solution prepared by dissolving 0.26 g of lithium trimethyl silanolate in 3 ml of dehydrated tetrahydrofuran, to which a solution prepared by dissolving 12.0 g of hexamethyl cyclotrisiloxane in 30 ml of dehydrated tetrahydrofuran was added to form a mixture. After agitation for four hours at room temperature, the mixture was further admixed with 0.864 g of 3-methacryloxypropyl dimethyl chlorosilane and agitated for 1 hour at room temperature.

Thereafter, the reaction mixture was freed from the precipitates of lithium chloride by filtration and the filtrate was admixed with methyl alcohol to form precipitates which were purified by the method of reprecipitation using tetrahydrofuran as the solvent and methyl alcohol as the precipitant. The thus obtained product was subjected to the analysis by the methods of gel-permeation chromatography and infrared absorption spectrophotometry to give the results shown below, from which the product was identified to be a dimethyl polysiloxane terminated at a single molecular chain end with a 3-methacryloxypropyl group. The dimethyl polysiloxane, however, had a much broader molecular weight distribution than in the product obtained in Example 2 as indicated by the value of $M_w/M_n$ shown below.

Molecular weight by gel-permeation chromatography (reference made to polystyrenes)

$M_n$: 6500
$M_w$: 7350
$M_w/M_n$: 1.13

Infrared absorption spectrophotometry 1000–1100 cm$^{-1}$ (Si—O—Si) 1260 cm$^{-1}$ (Si—C) 1720 cm$^{-1}$ (C=O)

What is claimed is:

1. A method for the preparation of an organopolysiloxane ethylenically polymerizable only at a single molecular chain end represented by the general formula $$R_3Si-O-(-SiR_2-O-)_{n+1}-SiMe_2-R^2-O-CO-CR^1=CH_2,$$

in which Me is a methyl group, R is, each independently, an alkyl group having 1 to 6 carbon atoms or a phenyl group, $R^1$ is a hydrogen atom or a methyl group, $R^2$ is a divalent hydrocarbon group having 1 to 6 carbon atoms and n is zero or a positive integer not exceeding 1000, which comprises:

reacting an organopolysiloxane having a silanolic hydroxy group only at a single molecular chain end as represented by the general formula $$R_3Si-O-(-SiR_2-O-)_n-SiR_2-OH,$$

in which each symbol has the same meaning as defined above, with an ω-(meth)acryloxyalkyl dimethyl dialkylamino silane compound represented by the general formula $$R^3_2N-SiMe_2(R^2-O-CO-CR^1=CH_2),$$

in which Me, $R^1$ and $R^2$ each have the same meaning as defined above and $R^3$ is an alkyl group having 1 to 6 carbon atoms.

2. The method for the preparation of an organopolysiloxane ethylenically polymerizable only at a single molecular chain end as claimed in claim 1 in which $R^3$ is a methyl group or ethyl group.

3. The method for the preparation of an organopolysiloxane ethylenically polymerizable only at a single molecular chain end as claimed in claim 1 in which the ω-(meth)acryloxyalkyl dimethyl dialkylamino silane compound is admixed in an amount of 1.0 to 1.5 moles with mole of the organopolysiloxane having a silanolic hydroxy group only at a single molecular chain end.

4. The method for the preparation of an organopolysiloxane ethylenically polymerizable only at a single molecular chain end as claimed in claim 1 in which the mixture of the ω-(meth)acryloxyalkyl dimethyl dialkylamino silane compound and the organopolysiloxane having a silanolic hydroxy group only at a single molecular chain end is admixed with an organic solvent having no active hydrogen.

5. The method for the preparation of an organopolysiloxane ethylenically polymerizable only at a single molecular chain end as claimed in claim 1 in which the mixture of the ω-(methyl)acryloxyalkyl dimethyl dialkylamino silane compound and the organopolysiloxane having a silanolic hydroxy group only at a single molecular chain end is heated at a temperature in the range from 50° to 70° C.

* * * * *